United States Patent
Shippert

(10) Patent No.: US 6,786,883 B2
(45) Date of Patent: Sep. 7, 2004

(54) APPLICATOR FOR INSERTION OF CARGO INTO A BODY CAVITY

(76) Inventor: Ronald D. Shippert, 4975 S. Albion St., Littleton, CO (US) 80121

(*) Notice: Subject to any disclaimer, the term of this patent is extended or adjusted under 35 U.S.C. 154(b) by 69 days.

(21) Appl. No.: 10/123,487

(22) Filed: Apr. 15, 2002

(65) Prior Publication Data

US 2003/0195459 A1 Oct. 16, 2003

(51) Int. Cl.[7] ............................................. A61F 13/20
(52) U.S. Cl. ................................. 604/15; 604/385.18
(58) Field of Search .................. 604/11–18, 57–60, 604/311, 385.17, 385.18

(56) References Cited

U.S. PATENT DOCUMENTS

| | | | |
|---|---|---|---|
| 636,637 A | 11/1899 | Cooke | |
| 940,519 A | * 11/1909 | Eastman | |
| 1,969,671 A | * 8/1934 | Nelson | |
| 2,351,836 A | * 6/1944 | Popper | |
| 2,509,241 A | * 5/1950 | Mende | 604/11 |
| 3,059,642 A | * 10/1962 | Gershen | |
| 3,068,867 A | 12/1962 | Bletzinger et al. | |
| 3,204,635 A | * 9/1965 | Voss et al. | |
| 3,433,225 A | 3/1969 | Voss et al. | |
| 3,570,494 A | 3/1971 | Gottschalk | 128/325 |
| 3,674,026 A | 7/1972 | Werner et al. | 128/263 |
| 3,717,149 A | 2/1973 | Morane | |
| 3,753,437 A | * 8/1973 | Hood et al. | |
| 3,759,258 A | * 9/1973 | Loyer | |
| 3,850,176 A | 11/1974 | Gottschalk | 128/325 |
| 3,884,233 A | * 5/1975 | Summey | |
| 3,974,965 A | 8/1976 | Miller | 239/413 |
| 4,030,504 A | 6/1977 | Doyle | 128/325 |
| 4,048,998 A | * 9/1977 | Nigro | |
| 4,536,178 A | 8/1985 | Lichstein et al. | 604/15 |
| 4,573,964 A | * 3/1986 | Huffman | |
| 4,755,166 A | 7/1988 | Olmstead | 604/11 |
| D298,653 S | 11/1988 | Maietta | D24/63 |
| 4,895,559 A | 1/1990 | Shippert | 604/15 |
| 4,900,315 A | 2/1990 | Lundqvist et al. | 604/311 |
| 5,127,552 A | 7/1992 | Bauman et al. | 222/145 |
| 5,395,309 A | 3/1995 | Tanaka et al. | 604/18 |
| 5,507,807 A | * 4/1996 | Shippert | 623/8 |
| 5,601,077 A | 2/1997 | Imbert | 128/200.14 |
| 5,700,252 A | 12/1997 | Klingenstein | 604/280 |
| 5,702,362 A | 12/1997 | Herold et al. | 604/58 |
| 5,709,652 A | * 1/1998 | Hagerty | |
| 6,186,973 B1 | * 2/2001 | Buzot | |
| 6,264,626 B1 | 7/2001 | Linares et al. | 604/15 |
| 6,322,531 B1 | 7/2001 | Linares et al. | 604/15 |
| 6,508,780 B1 | * 1/2003 | Edgett et al. | |

* cited by examiner

Primary Examiner—John J. Calvert
Assistant Examiner—Linh Truong
(74) Attorney, Agent, or Firm—Sheridan Ross P.C.

(57) ABSTRACT

An applicator for insertion of cargo into a body cavity is provided. The applicator includes an applicator body having a number of walls and at least one breach. Greater flexibility in the applicator body is achieved due to the breach. This flexibility of the applicator body enables cargo to be desirably held in a holding space of the applicator body until it is to be inserted into the body cavity. During insertion, a plunger engages the cargo and pushes it from the applicator body. The flexibility of the applicator body walls facilitates the movement of the cargo. The breach can be located or formed in various positions including along intersections of applicator body walls, intermediate applicator body walls, as an open wall, as well as continuously along substantially the entire length of the applicator body. In one embodiment, the applicator is configured to securely hold the applicator body and the plunger together.

18 Claims, 6 Drawing Sheets

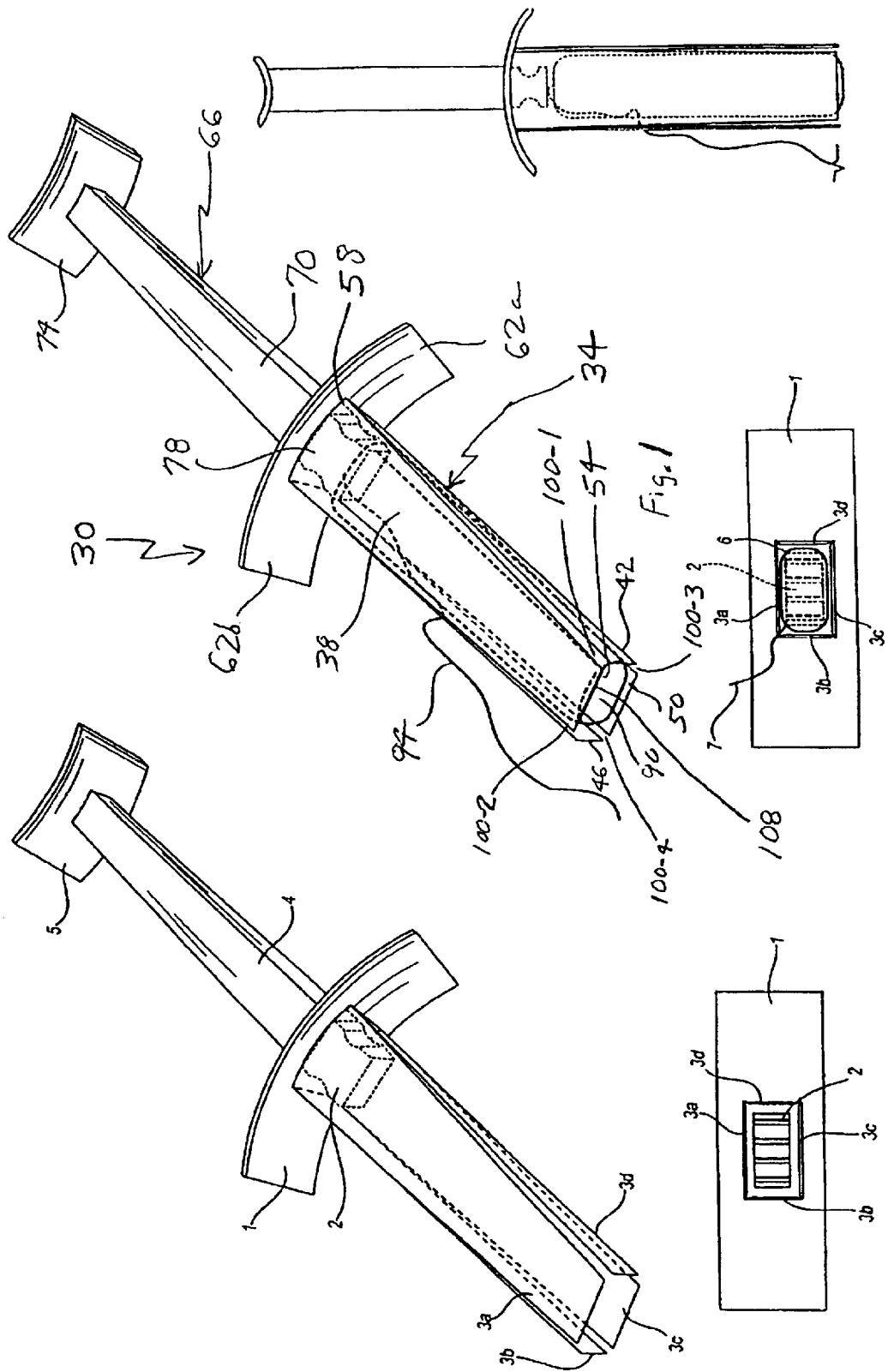

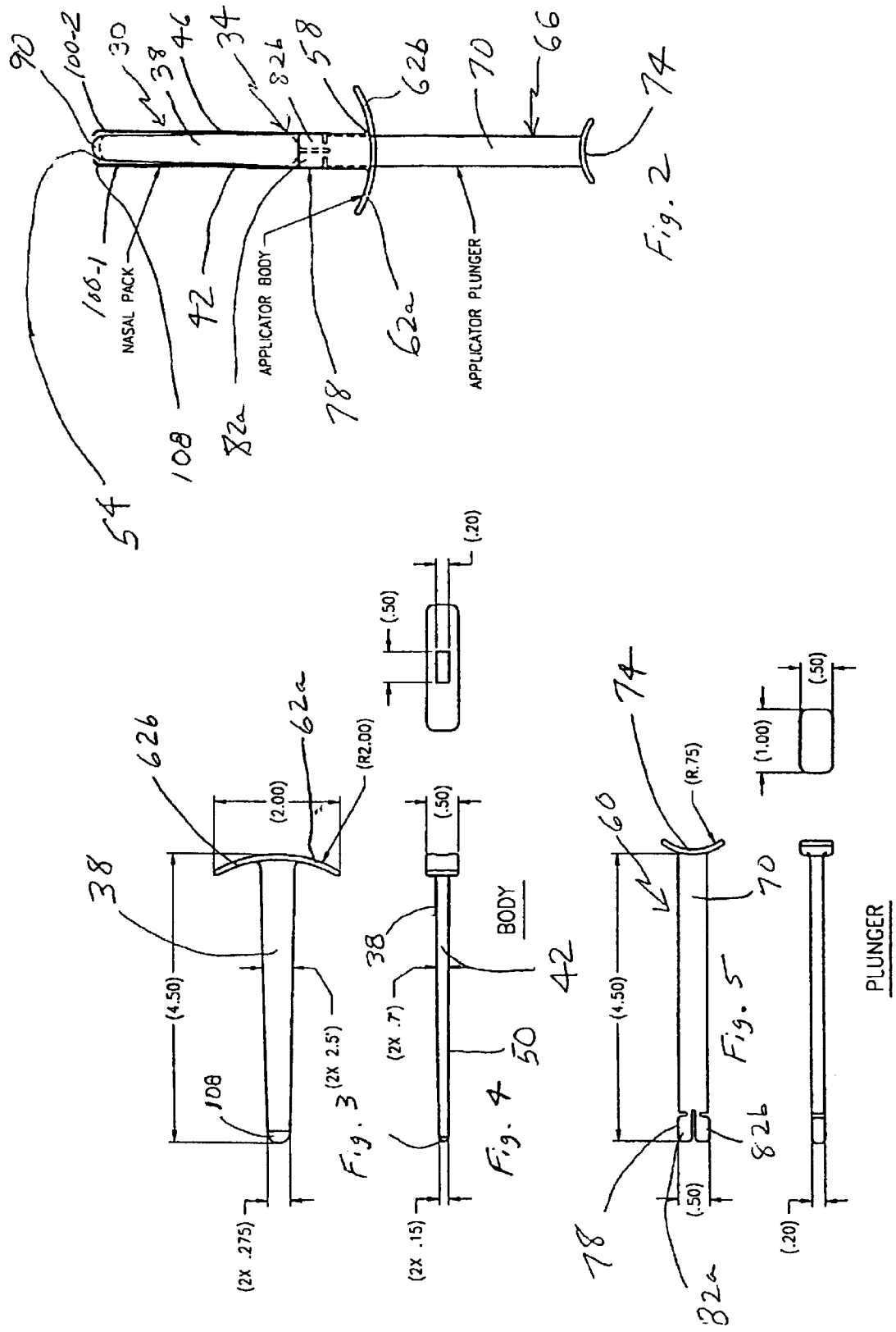

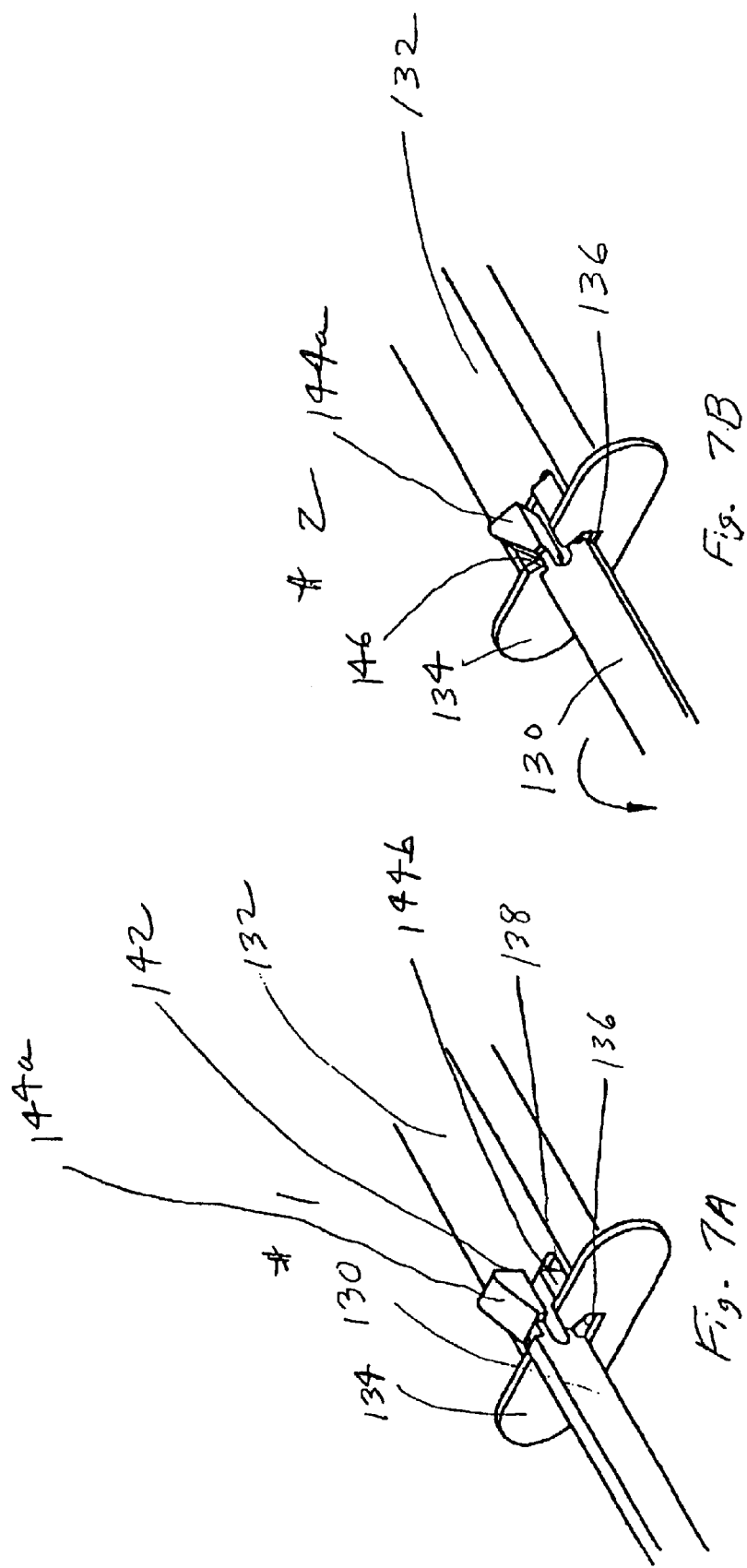

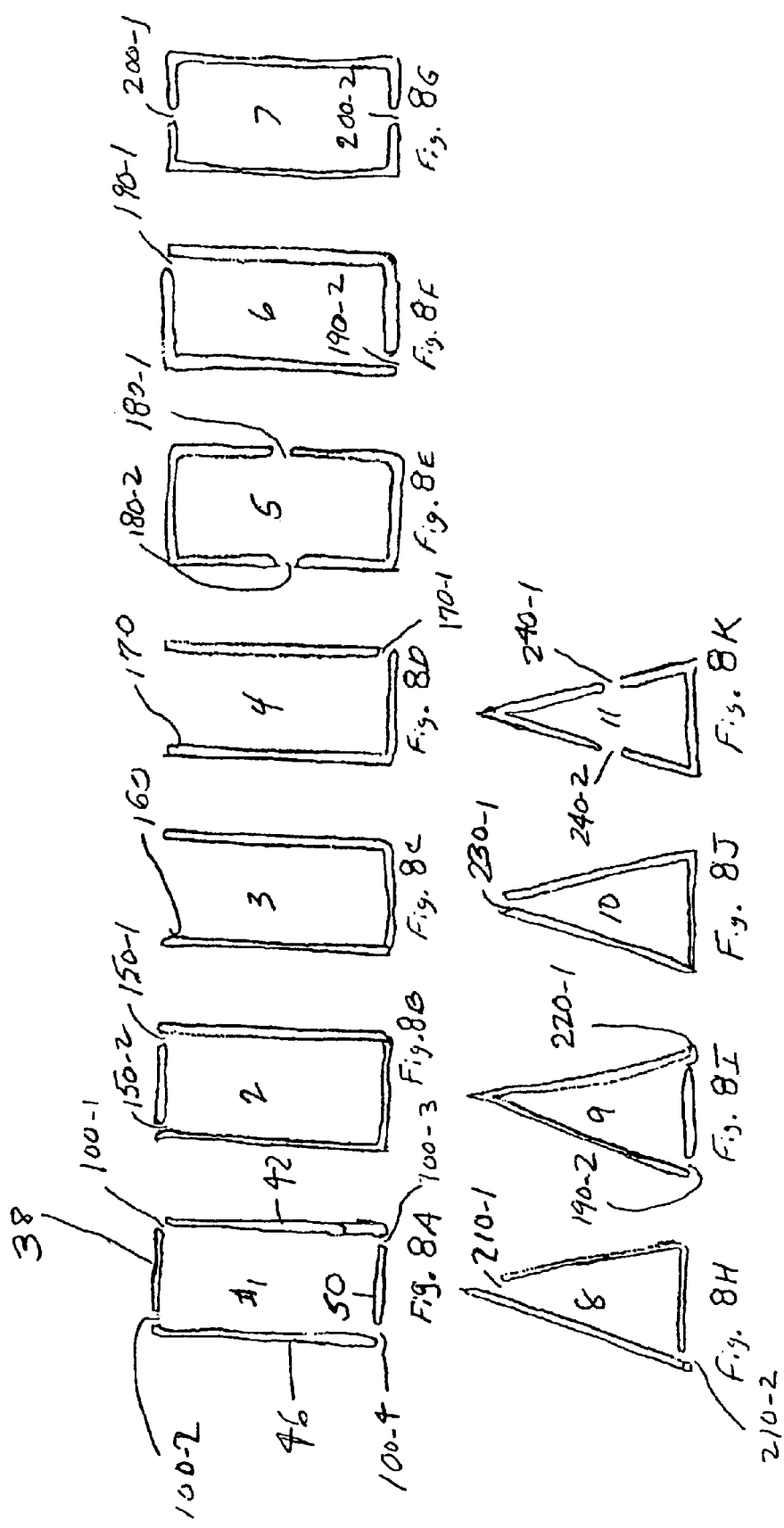

APPLICATOR FOR INSERTION OF CARGO INTO A BODY CAVITY

FIELD OF THE INVENTION

The present invention relates to an applicator for inserting a cargo, such as absorbent, into a body cavity.

BACKGROUND OF THE INVENTION

Numerous insertion devices have been advanced for positioning a liquid absorbent member into a body cavity. Some of these devices are in the form of a syringe-like product having a body configured to hold an absorbent member and a plunger that is used to push the absorbent member from the body into the body cavity. These syringe-like products may have one or more of drawbacks. In particular, these prior art devices may not be configured for desired holding of a variety of sizes of absorbents. In such a case, the user is limited to absorbents having specific sizes with strict tolerances. Such products may not be dimensionally configured for the body cavity into which the absorbent is to be placed. There may also be more difficulty in achieving the removal of the absorbent from the device. Additionally, these prior art products may be deficient in providing anatomically desirable portions for handling or gripping by the user.

SUMMARY OF THE INVENTION

In accordance with the present invention, an applicator is provided for inserting a cargo or material, such as an absorbent, into a selected body cavity. In one embodiment, the body cavity can be a nasal cavity or a sinus cavity in the nose of a human patient. In other embodiments, the cavity may be an animal cavity already present or later formed in an animal. The applicator includes a body, the material or cargo to be inserted into the body cavity and a plunger that is used in pushing the cargo from the applicator body into the body cavity.

The applicator body is elongated and defines a body length. The applicator body can have different shapes including rectangular, square or triangular in cross-section. The applicator body has a number of walls that come or join together at wall intersections. At least one breach or opening is formed in the applicator body. The breach has a total length that is equal to at least one-half of the applicator body length. The breach total length may be continuous or discontinuous along the applicator body length. In a preferred embodiment, the breach is continuous along at least one-half of the applicator body length. Even more preferably, the total length of the breach is equal to, or substantially equal to, the entire applicator body length. Regardless of its total length, the breach can be formed essentially at the intersection of two of the walls of the applicator body. In another embodiment, at least one breach is formed intermediate of two wall intersections, e.g., along the mid portions of the longitudinal extent of one wall. In still another embodiment, the opening or breach is defined by a missing or "open" wall that results in the applicator body having a cross-section along its length in the form of a U-shape.

The applicator body can also have different configurations associated with its length. In one embodiment, one or more of the applicator body walls has a thickness that is greater at the proximal end of the applicator body than the thickness at its distal end. In the same or another embodiment, one or more of the applicator body walls inclines at an angle from its proximal end to its distal end.

The plunger has a plunger body and a gripping or engaging element or elements provided at its proximal end. In one embodiment, the engaging element is curved in such a way to provide an anatomically desirable pushing surface. This surface is more conveniently or comfortably engaged by the user in connection with imparting a force to the plunger in order to move an absorbent from the holding space defined by the walls of the applicator body. In that regard, the absorbent is positioned in the holding space. The size and dimensions of the absorbent are suitably matched to the size and dimensions of the holding space so that the absorbent is properly held or maintained in the holding space until it is moved therefrom using the plunger. The one or more breaches provide advantageous flexibility in the one or more walls of the applicator body whereby the applicator body walls constrict or prevent unwanted movement or escape of the absorbent from holding space of the applicator body. Conversely, this flexibility facilitates removal of the absorbent from the applicator holding space into the body cavity when the plunger is used to engage and move the absorbent from the open end of the applicator body.

In one embodiment, the absorbent or other cargo has a string attached to it. The string can be useful in later removal of the cargo from a body cavity. When the string is part of the cargo, it is important that the string not bind against the inside or inner surface of one or more of the applicator body walls when the cargo is to be inserted into the body cavity. This unwanted binding can be avoided using the flexibility associated with the one or more applicator body walls in which at least one of them can move outwardly at least to some degree as the cargo is pushed from the applicator body so that there is sufficient room for the string and no unwanted binding or engagement between the string and any inside surface of an applicator body wall. In the embodiment in which the breach constitutes or is defined by an open applicator body wall, the absorbent can be positioned in the holding space defined by the other structural walls of the applicator body such that the string is adjacent to this open wall. Accordingly, when the absorbent is pushed from the applicator body, the string is open or exposed to the open wall and no binding thereof occurs.

In one embodiment that can be implemented even when there is no breach, the applicator body has at least a first or gripper hole and the plunger has a tip. The tip has a longitudinal extent and a lateral extent. The tip is resilient to be extendable to have its longitudinal extent greater than the longitudinal extent of the gripper hole and/or its lateral extent greater than the lateral extent of the gripper hole. To position the tip into the holding space of the applicator body the longitudinal extent of the tip can be aligned with the lateral extent of the gripper hole but cannot be aligned with its longitudinal extent. Once in this desired alignment, the plunger including its tip are rotated relative to a second or applicator body or shaft hole to be received therein and for positioning in the holding space. A third hole or notch communicates with both the gripper hole and the shaft hole and receives portions of the tip's lateral extent.

Based on the foregoing summary, a number of advantages of the present invention are readily discerned. An applicator is provided that includes a holding space for properly or tightly holding cargo before it is inserted into a body cavity. The applicator body has one or more breaches that facilitate removal of the cargo due to the flexibility in the one or more walls as result of the breach or breaches. The applicator body can have different designs, particularly in cross-section, in order that there is a better conforming or accommodation related to the shapes of the body cavity into which the cargo is to be received. The plunger has an engaging element that enhances handling or moving the plunger in connection with insertion of the cargo into the body cavity. The applicator body and the plunger can be sized to securely hold them together at all times after assembly so there is no concern about unwanted separation of these two parts. The cargo itself can have a variety of sizes and shapes and the tolerances and/or ranges associated therewith can be increased for a particular applicator due to the flexibility of the applicator body in maintaining the cargo and removal thereof when desired.

Additional advantages of the present invention will become readily apparent from the following discussion, particularly when taken together with the accompanying drawings.

BRIEF DESCRIPTION OF THE DRAWINGS

FIG. 1 is a perspective view of an applicator of the present invention;

FIG. 2 is a top view of the applicator of FIG. 1;

FIG. 3 is a top view of the applicator body of FIG. 2;

FIG. 4 is a side view of the applicator body;

FIG. 5 is a top view of the plunger of FIG. 2;

FIG. 7A illustrates a fragmentary, perspective view of an applicator in which the applicator body and the plunger are configured to be securely held together before use of the applicator and thereby avoid separation of the applicator body and plunger;

FIG. 7B is a fragmentary perspective view, similar to FIG. 7A, illustrating rotation of the plunger body tip in connection with securing the plunger and the applicator body together;

FIG. 8A diagrammatically illustrates a generally rectangular cross-section of an applicator body having four breaches at the corners or wall intersections;

FIG. 8B diagrammatically illustrates a generally rectangular cross-section of an applicator body showing two breaches at the top wall along the two wall intersections;

FIG. 8C diagrammatically illustrates a cross-section of an applicator body having an open or missing wall that defines a U-shape;

FIG. 8D diagrammatically illustrates an applicator body cross-section having an open top wall and a breach at an intersection with the bottom wall;

FIG. 8E diagrammatically illustrates a generally rectangular cross-section of an applicator body having two breaches extending along mid portions of the side walls;

FIG. 8F diagrammatically illustrates a generally rectangular cross-section of an applicator body having diagonal breaches at wall intersections;

FIG. 8G diagrammatically illustrates a generally rectangular cross-section of an applicator body having two breaches along mid portions of top and bottom walls;

FIG. 8H diagrammatically illustrates a generally triangular cross-section of an applicator body having one breach at the apex and another breach at the base;

FIG. 8I diagrammatically illustrates a generally triangular cross-section of an applicator body having two breaches at the base;

FIG. 8J diagrammatically illustrates a generally triangular cross-section of an applicator body having a breach at the apex; and FIG. 8K diagrammatically illustrates a generally triangular cross-section of an applicator body having breaches along substantially the mid portions of the side walls.

DETAILED DESCRIPTION

Figure 6:
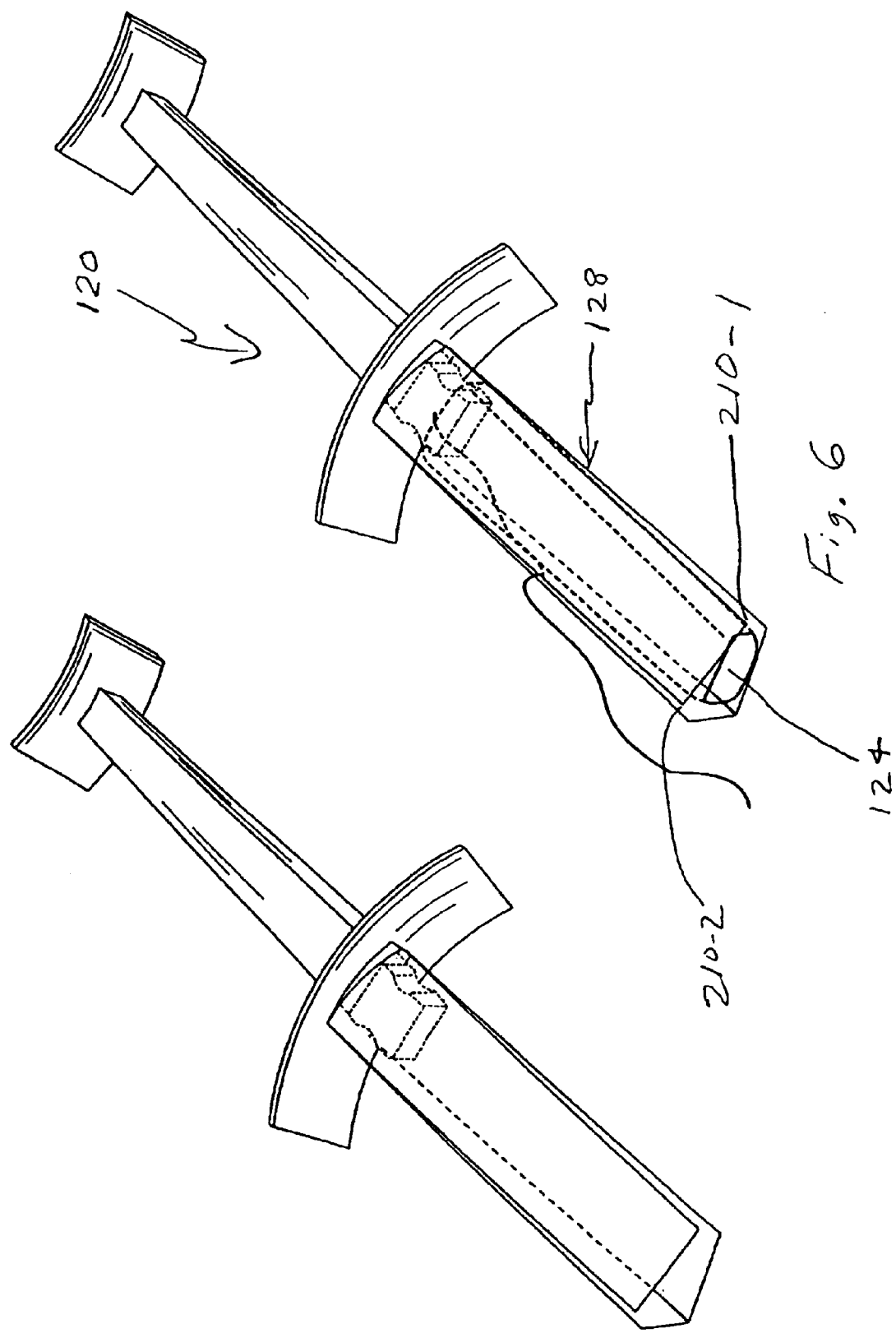
FIG. 6 is a perspective view of another embodiment of an applicator that has an applicator body with a generally triangular cross-section.

With reference to FIGS. 1–5, an applicator 30 is illustrated for use in inserting a cargo into a human body cavity or animal cavity. The cavity can be virtually any open area or volumetric space that is naturally present or later created, such as those associated with the ear, eye, sinus, subcutaneous tissue or operative sites. The cargo can be of numerous and different sizes and can include fluid absorbents, packs, suppositories, solid type medication, medicinals, electronic devices or implants.

The applicator 30 includes an applicator body 34 having a number of walls. Without intending to limit the orientation of the applicator body 34, it can include a top wall 38, a first side wall 42 and a second side wall 46, as well as a bottom wall 50. The applicator body 34 has an open end 54 and a gripping end 58. At the gripping end 58, a digit gripping piece is provided that can be defined as being comprised of first and second gripping elements 62a, 62b. Each of the two gripping elements 62a, 62b is curved inwardly towards the remaining portions of the applicator body and the open end 54.

The applicator 30 also includes an applicator plunger 66 comprising a plunger body 70 with a pusher element 74 at a proximal end thereof and a tip 78 at a distal end thereof. The pusher element 74 is curved and has a radius associated therewith of a dimension to readily and comfortably receive a digit, such as the thumb, of the user or operator in connection with pushing or moving the applicator plunger 66. During the insertion process, the pusher element 74 is engaged and pushed to cause relative movement between the applicator plunger 66 and the applicator body 34. The tip 78 can be comprised of a pair of wings 82a, 82b that enable the tip 78 to be compressed and later expanded after placement within the cargo receiving or holding space of the applicator body 34. The receiving space of the applicator body 34 can hold the cargo 90. In the embodiment of FIG. 1, the cargo 90 can be an absorbent that is able to absorb body fluids, such as blood present in a cavity. The absorbent of FIG. 1 has a string 94 connected to it that can be useful in facilitating removal of the absorbent from the cavity after use.

Important to the present invention relates to providing the applicator body 34 with sufficient flexibility to facilitate placement and removal of the cargo 90 relative to the applicator body 34. When inserting the cargo 90 into a body cavity, it is desirable that removal of the cargo 90 be as smooth as reasonably possible. Furthermore, it is desirable that small variations in cargo dimensions be accommodated so that the same applicator 30 can be used with different size cargo without concern of meeting tight tolerance requirements. This flexibility can be achieved through the capability of one or more of the applicator body walls being able to move outwardly when the cargo 90 is being inserted into a body cavity. Preferably, in order to provide the flexibility, one or more breaches are formed or otherwise defined in the applicator body walls. A breach associated with one or more of the applicator body walls can take many forms including separations along the intersections of the walls, separations in the walls, an open wall (wall is removed or missing), as well as such breaches having different lengths and/or widths. Each breach has a total length, which may be continuous or discontinuous along the length of the applicator body. Preferably, the total length is at least a majority of the applicator body length. A breach can be continuous from adjacent the gripping or proximal end 58 of the applicator body 34 and extend continuously to the open end 54 of the applicator body 34.

In the embodiment of FIGS. 1–5 and 8A, there are four breaches 100-1, 100-2, 100-3, and 100-4. The breach 100-1 is formed at the intersection of the top wall 38 and the first sidewall 42. The breach 100-2 is formed at the intersection of the top wall 38 and second side wall 46. The third breach 100-3 severs the bottom wall 50 from the first side wall 42 such that the third breach 100-3 is found at the intersection of these two walls. Similarly, the fourth breach 100-4 severs the bottom wall 50 from the second side wall 46 such that the fourth breach 100-4 is found at the intersection of these two walls. In one embodiment, each of these breaches 100-1 . . . 100-4 extends at least substantially from the open end 54 continuously to the proximal end 58 of the applicator body 34 adjacent to the gripping elements 62a, 62b. In another embodiment, one or more of these breaches 100-1 . . . 100-4 may not be continuous along the length of the applicator body 34.

In addition to the flexibility of the applicator body walls, further dimensional related aspects are provided to enhance holding of the cargo 90 in the body receiving volume or holding space within or defined by the applicator body walls. In one or more embodiments, the applicator 30 can include one or more applicator body walls that taper inwardly starting from adjacent the proximal end 58 of the applicator body 34 towards its open or distal end 54. The thickness of one or more of the applicator body walls can also change from the proximal end 58 to the open end 54 of the applicator body 34. The thickness of one or more of the body walls can be greater adjacent to the proximal end 58 and then decrease or become thinner and be more thin adjacent to the open end 54. The tip 108 at the open end 54 of the applicator body 34 can also be tapered or curved inwardly thereby closing off portions of the open end 54 that reduces the opening over that which should otherwise exist but for such a tapered tip 108. Each of any of these possible dimension attributes can be incorporated to better hold the cargo 90 while it is being held in the applicator body receiving space and yet allow for proper removal of the cargo 90 from the applicator body 34 when it is being inserted into a body cavity.

With reference to FIG. 6, another embodiment of an applicator 120 is illustrated for insertion of a cargo 124 into a cavity. Instead of a generally rectangular or square cross-section, the applicator body 128 has a generally triangular cross-section. In this embodiment, two breaches are formed. A first breach 210-1 is provided at the apex of the triangular shape where two applicator body walls come together. A second breach 210-2 is provided at the base of the triangular shape where one of the side walls and the base wall intersect. Such a triangular shape is more beneficial when the cavity has a shape that is more like the triangular cross-section and/or where the cargo 124 has a more triangular cross-section shape. Like the embodiment of FIG. 1, the cargo 124 is illustrated as being an absorbent, although as previously described, many different and various forms of cargo can be utilized with the present invention.

Referring next to FIGS. 7A–7D, one or more applicators can include structure or a feature useful in securely holding a plunger 130 in an applicator body 132. Consequently, during shipping, when preparing to use the applicator or any other handling of the applicator does not result in separation between the plunger 130 and the applicator body 132. For example, the user of the applicator need not be concerned with locating the plunger 130 into the applicator body 132 since they are assembled together and the user need not be concerned with their separation when the user is preparing to insert the cargo into the cavity. The secure holding structure of this embodiment includes the applicator body 132 having a digit gripper 134 provided at its proximal end. The digit gripper 134 has a gripper hole 136 that can be formed in the body of the gripper 134 at its mid portions. The gripper 134 is also defined as including a notch 146 that communicates with the gripper hole 136 The applicator body 132 has a shaft hole 138 provided adjacent to its proximal end and in communication with the gripper hole 136. The plunger 130 includes a flexible tip 142. The flexible tip 142 can be constructed of a pair of movable prongs 144a, 144b with a gap in between. When the prongs 144a, 144b are fully extended, the tip 142 has a length or longitudinal extent and a width or a lateral extent. These two dimensions are less than the corresponding longitudinal and lateral extents of the gripper hole 136. In one embodiment, the longitudinal and lateral extents of the gripper hole 136 are 70–90% of the corresponding longitudinal and lateral extents of the tip 142 and, preferably, about 80% thereof. Because of these differences in sizes, the tip 142 cannot be inserted or positioned through the gripper hole 136 by alignment of corresponding longitudinal extents and corresponding lateral extents. That is, because the longitudinal extent of the tip 142 is greater than the longitudinal extent of the gripper hole 136, the plunger 130 cannot be positioned into the applicator body 132 when the longitudinal extent of the tip 142 is aligned with the longitudinal extent of the gripper hole 136.

Figure 7D:
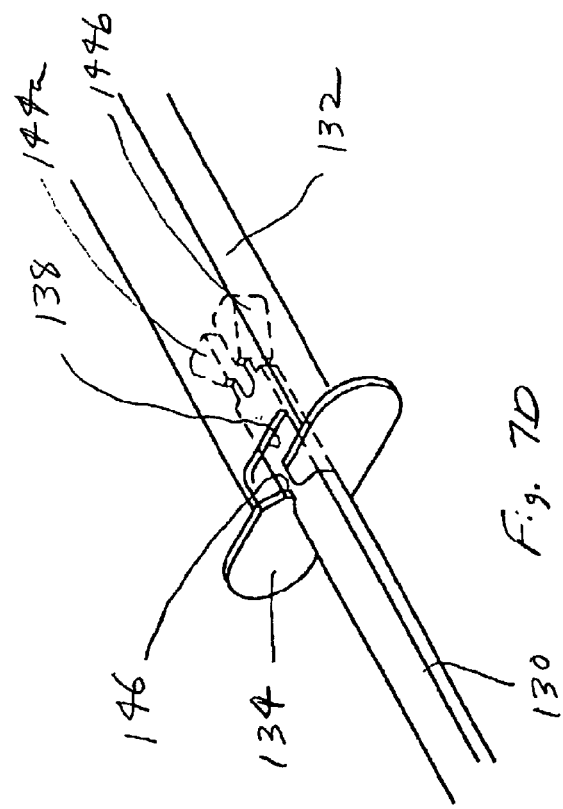
FIG. 7D is a fragmentary perspective view, similar to FIG. 7C, illustrating insertion of the plunger into the applicator body and the spreading of the tip of the plunger.
Figure 7C:
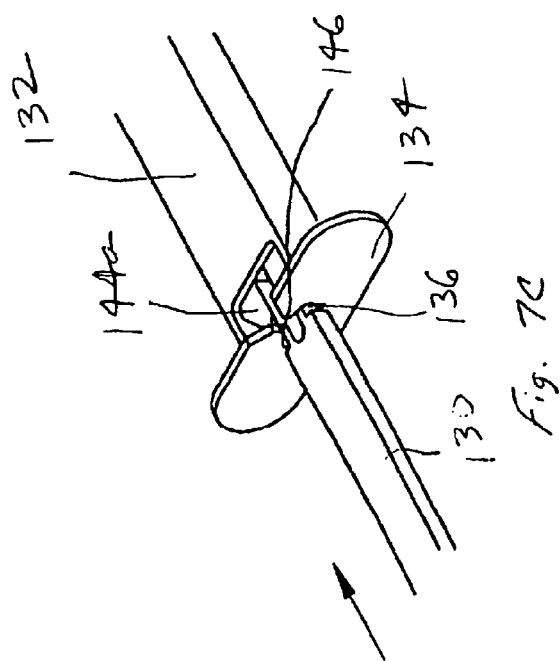
FIG. 7C is a fragmentary perspective view, similar to FIG. 7B, illustrating the completed rotation of the plunger relative to the applicator body.

To accomplish the insertion or joining of the plunger 130 to the applicator body 132, the lateral extent of the tip 142 is aligned with the longitudinal extent of the gripper hole 136. This is illustrated in FIG. 7A in which the plunger 130 is positioned so that the lateral extent of the tip 142 is located through the longitudinal extent of the gripper hole 136 until at least portions of the tip 142 occupy at least portions of the shaft hole 138 and at least other portions of the tip 142 occupy at least portions of the notch 146. To continue with the joining or assembling of the plunger 130 and the applicator body 132, the plunger 130 is rotated or turned so that the longitudinal extent of the tip 142 turns in a direction towards aligning with the longitudinal extent of the gripper hole 136. The shaft hole 138 has space to allow for such movement and receipt of additional portions of the tip 142. As seen in FIG. 7C, the rotation of the plunger 130 is completed such that the longitudinal extent of the tip 142 is aligned with the longitudinal extent of the gripper hole 136, but with the tip 142 located within the holding space of the applicator body 132. The plunger 130 and its accompanying tip 142 can be suitably located within the applicator body 132 and with the tip 142 in an extended position, as seen in FIG. 7D. In this position, since the longitudinal extent of the tip 142 is greater than the longitudinal extent of the gripper hole 136, the plunger 130 cannot slide from the applicator body 132 back through the gripper hole 136 or otherwise easily be removed therefrom. Instead, the same type of manipulation, in the reverse order, would have to be utilized in order to separate the plunger 130 from the applicator body 132. Thus, the plunger 130 is securely held within the applicator body 132.

In one or more similar embodiments, although one or more of these are not necessary for every embodiment, the following size related structures can be provided. The length of the plunger 130 and the length of the applicator body 132 are about the same. The body or shaft portion of the plunger 130 has a width and height that will be less than the width and height of the extendable tip 142. The length of the tip 142 is about 10% of the length of the entire plunger 130. The external dimensions of the body or shaft portions of the plunger 130 will be about the same as the internal dimensions of the gripper hole 136. The tip 142 will have about the same outside dimensions as the internal dimensions of the applicator body 132 at its gripper or proximal end. The lateral extent or width of the tip 142 will have about the same external dimensions as the width of the notch 146. The gripper hole 136 has about the same height and width as the height and width of the shaft or body portions of the plunger 130.

With reference to FIGS. 8B–8K, some other embodiments are illustrated related to a flexible wall applicator body 34. In FIG. 8B, breaches 150-1, 150-2 are provided at the two intersections of the top and side walls. These breaches 150-1, 150-2, like the breaches of FIG. 8A could extend continuously for substantially the entire length of the applicator body 34. FIG. 8C illustrates the breach 160 in the form of an open wall (missing wall) so that the rectangular-shaped cross-section shows three walls for the applicator body 34 instead of four walls. FIG. 8D is similar to FIG. 8C in that it includes an open wall 170 at the top of the applicator body 34. Additionally, a breach 170-1 is provided at the intersection of a first side wall and the bottom wall. Referring next to FIG. 8E, there are two breaches 180-1, 180-2, with one being formed in each of the first and second sidewalls, respectively. The breach 180-1 is intermediate, preferably at about the mid-portions, of the wall intersections of the top wall and the first side wall and the bottom wall and the first side wall. The breach 180-2 is intermediate the intersections of the top wall and the second side wall and the bottom wall and the second side wall. FIG. 8F depicts the breach 190-1 at the intersection of the top wall and the first side wall and the breach 190-2 at the intersection of the bottom wall and the second side wall (diagonal breaches). FIG. 8G illustrates intermediate breaches 200-1, 200-2. Instead of the side walls, the breach 200-1 is in the top wall intermediate the wall intersections of the top wall and the first and second side walls. The breach 200-2 is in the bottom wall intermediate the wall intersections of the bottom wall and the first side wall and the bottom wall and the second side wall. FIG. 8H illustrates a different geometric shape. Instead of rectangular or square, the lateral section is triangular in shape. This embodiment has two breaches 210-1, 210-2. The first breach 210-1 is provided adjacent the apex of the triangular shape and the second breach 210-2 is provided at the intersection of the base wall and a side wall. FIG. 8I is also triangular in shape and has two breaches 220-1, 220-2. These two breaches are formed at opposite ends of the base wall at its intersections with the two side walls. FIG. 8J includes the single breach 230-1 at the apex of the triangular shape. FIG. 8K has the breaches 240-1, 240-2 formed intermediate the wall intersections and spaced from each the base wall and the apex. As can be appreciated, a substantial number and variety of breaches can be provided in other embodiments as well in connection with achieving the desired flexibility of the applicator body walls.

Further detailed information is next provided related to the dimensions and uses of the applicator 30. With respect to the thickness of the applicator body 34, in one embodiment, its thickness adjacent to the proximal end 58 is about 0.050 inch, plus or minus 0.010 inch and the thickness of the applicator body 34 at its distal end is about 0.020 inch, plus or minus 0.005 inch. Regarding the tapering of one or more applicator body walls to define wall angles, the angle of tilt inward of the first and second side walls is about 1.250 degrees and the angle of tilt inward of the top and bottom walls is about 0.350 degrees, with the side walls in the rectangular cross-section typically being more wide than the top and bottom walls.

With regard to cargo size and the types of cargo, the cargo can be characterized as having a generally rectangular or square shape or a generally triangular shape. For each of these two general shapes, each can be further characterized as having a nasal pack application, a large model application and a small model application. Referring first to the nasal pack having a rectangular shape, it can be used for delivery of packs of absorbents, suppositories and solid type medication into the nose. The height of such cargo can range in size from 0.250 inch to 0.700 inch and the height is preferably about 0.500 inch. The width of this cargo is in the range of 0.100 inch to 0.300 inch and preferably about 0.200 inch. The height of this cargo at its tip is in the range of 0.200 to 0.350 inch and preferably about 0.275 inch. The width of the cargo at its tip is in the range or 0.100 to 0.200 inch and preferably about 0.150 inch. Its length is in the range of 3–6 inches and preferably about 4.5 inches. The rectangular small model of cargo can typically include electronic devices, packs, medicinals or implants into the ear, eye, sinus, subcutaneous tissue or small operative sites.

The rectangular shaped large model typically includes cargo in the form of electronic devices, packs, medicinals, or implants into larger areas such as the breast, rectum, vagina and larger operative sites. These small and large model rectangular shaped cargos are encompassed in the following ranges. The height of the cargo at its base is in the range of 0.250–2.00 inches. Its width at this base end is in the range of 0.100–0.800 inch. At the tip end of this cargo, its height is in the range of 0.200–2.00 inch and its width at the tip end is in the range of 0.078–0.800 inch. The range of the lengths for these rectangular shaped large and small models is between 2–9 inches.

Describing next dimensional information related to the triangular shape cargo, for the nasal model used in providing cargo into the nose, the height at the base end of the cargo is in the range of 0.250–0.700 inch and preferably about 0.500 inch. The cargo width at its base end is in the range of 0.100–0.300 inch and preferably about 0.200 inch. The height at the tip end for this triangular shape cargo is in the range of 0.200–0.350 inch and preferably about 0.275 inch. The width at the tip end is in the range of 0.100–0.200 inch and preferably about 0.150 inch. The cargo length is in the range of 3–6 inches and has a nominal or preferred length of about 4.5 inches.

Regarding the dimensional ranges for the triangular shape that encompasses both the small and large body models, the height at the base end is in the range of 0.500–2.00 inches and preferably about 1.0 inch. The width at the base end is in the range of 0.300–0.500 inch and preferably about 0.400 inch. The height for the triangular shaped head and body models at the tip end is in the range of 0.450–2.00 inches and preferably about 1.00 inch. The range for the width at the tip end is 0.200–0.800 inch and preferably about 0.400 inch. The cargo length is in the range of 3–9 inches and the nominal or preferred length is about 4.5 inches.

The foregoing discussion of the present invention has been presented for purposes of illustration and description.

Furthermore, the description is not intended to limit the invention to the forms disclosed herein. Consequently, further variations and modifications commensurate with the above teachings, within the skill and knowledge of the relevant art are within the scope of the present invention. The embodiments described hereinabove are further intended to explain the best mode presently known for practicing the invention and to enable others skilled in the art to utilize the invention in such, or in other, embodiments and with various modification(s) required by the particular application or use of the invention. It is intended that the appended claims be construed to include alternative embodiments to the extent permitted by the prior art.

What is claimed is:

1. An applicator for inserting a cargo into a body cavity, comprising:
   an applicator body having a proximal end and a distal end with a length therebetween and comprising a number of walls including at least first and second walls that define a holding space, a first breach formed in said applicator body and a second breach formed in said applicator body, each of said first and second breaches separating one of: (a) said first wall from said second wall and (b) portions of one of said first and second walls from other portions of said one of said first and second walls, wherein a total length of each of said first breach and said second breach is equal to at least one-half of said applicator body length, said first breach includes a separation between said first and second walls and that extends substantially continuously along said applicator body length;
   a cargo held in said holding space; and
   a plunger for moving said cargo from said body holding space;
   wherein said one of (a) and (b) remains separated including when said cargo is moved from said body holding space to the body cavity.

2. An applicator for inserting a cargo into a body cavity, comprising:
   an applicator body having a proximal end and a distal end with a length therebetween and including three walls that define a holding space and a breach formed in said applicator body that includes an open wall, said three walls being all walls of said applicator body, a cross-section of said applicator body immediately adjacent to said distal end has a substantially non-curved, U-shape, wherein a total length of said breach is equal to at least one-half of said applicator body length;
   a cargo held in said holding space; and
   a plunger for moving said cargo from said body holding space, said cargo has a string positioned adjacent to said open wall when said cargo is moved from said holding space using said plunger.

3. An applicator for inserting a cargo into a body cavity, comprising:
   an applicator body having a proximal end and a distal end with a length therebetween and including a number of walls that define a holding space and a breach formed in said applicator body, said number of walls define a substantially triangular-shaped cross-section and wherein a total length of said breach is equal to at least one-half of said applicator body length;
   a cargo held in said holding space; and
   a plunger for moving said cargo from said body holding space.

4. An applicator for inserting a cargo into a body cavity, comprising:
   an applicator body having a proximal end and a distal end with a length therebetween and including a number of walls that define a holding space and a breach formed in said applicator body, at least one of said walls has a thickness that is greater at said proximal end than said distal end and wherein a total length of said breach is equal to at least one-half of said applicator body length;
   a cargo held in said holding space; and
   a plunger for moving said cargo from said body holding space.

5. An applicator for inserting a cargo into a body cavity, comprising:
   an applicator body having a proximal end and a distal end with a length therebetween and including a number of walls that define a holding space and a breach formed in said applicator body, at least one of said walls inclines at an angle from said proximal end to said distal end so that said holding space is greater at said proximal end than said distal end and wherein a total length of said breach is equal to at least one-half of said applicator body length;
   a cargo held in said holding space; and
   a plunger for moving said cargo from said body holding space.

6. An applicator, as claimed in claim 1, wherein:
   said first breach is located along an intersection of said first and second walls.

7. An applicator, as claimed in claim 1, wherein:
   said first breach is located intermediate said first wall.

8. An applicator, as claimed in claim 1, wherein:
   said first breach is continuous for said total length.

9. An applicator, as claimed in claim 1, wherein:
   said cargo includes an absorbent with string and at least one of said walls is flexible and in which, in the absence of said at least one flexible wall, said string binds against said body when said plunger pushes against said cargo.

10. An applicator, as claimed in claim 1, wherein:
    said applicator body has at least a first digit engaging element that is substantially curved.

11. An applicator, as claimed in claim 1, wherein:
    said plunger has a curved part at a proximal end thereof.

12. An applicator, as claimed in claim 1, wherein:
    at least one of said walls flexes outwardly along at least said at least one-half of said body length during at least some movement of said cargo from said holding space.

13. An applicator, as claimed in claim 1, wherein:
    said total length of said first breach is in the range of between said one-half of said body length and substantially all of said applicator body length and in which said first breach is continuous.

14. An applicator for inserting a cargo into a body cavity, comprising:
    an applicator body having a proximal end and a distal end with a length therebetween and comprising a number of walls including at least first and second walls that define a holding space, a first breach formed in said applicator body and a second breach formed in said applicator body, each of said first and second breaches separating one of: (a) said first wall from said second wall; (b) portions of one of said first and second walls from other portions of said one of said first and second walls, wherein a total length of each of said first breach and said second breach is equal to at least one-half of said applicator body length;

a cargo held in said holding space; and a plunger for moving said cargo from said holding space and in which said applicator body has a gripper hole with a longitudinal extent and a lateral extent and said plunger has a tip with a longitudinal extent and a lateral extent, at least one of said longitudinal extent and said lateral extent of said tip being greater than said longitudinal extent and said lateral extent of said gripper hole, respectively, and in which said tip is uninsertable into said holding space when said longitudinal extent of said tip is aligned with said longitudinal extent of said gripper hole;

wherein said one of (a) and (b) remains separated including when said cargo is moved from said body holding space to the body cavity.

15. A method for joining a plunger to an applicator body of an applicator that has a holding space for receiving a cargo, comprising:

providing an applicator body having a gripper hole with a longitudinal extent and a lateral extent;

providing a plunger having a tip with a longitudinal extent and a lateral extent; and joining said plunger to said applicator body wherein, during said joining, said longitudinal extent of said tip is offset from said longitudinal extent of said gripper hole and said joining includes rotating said plunger tip to align said longitudinal extent thereof with said longitudinal extent of said gripper hole.

16. A method for joining a plunger to an applicator body of an applicator that has a holding space for receiving a cargo, comprising:

providing an applicator body having a gripper hole with a longitudinal extent and a lateral extent;

providing a plunger having a tip with a longitudinal extent and a lateral extent; and joining said plunger to said applicator body wherein, during said joining said longitudinal extent of said tip is offset from said longitudinal extent of said gripper hole, said applicator body includes a notch in communication with said gripper hole and a shaft hole in communication with said gripper hole, said joining includes locating portions of said lateral extent of said tip in said notch and rotating said tip for changing a position of said tip relative to said shaft hole.

17. An applicator, as claimed in claim 1, wherein said applicator body is without curves.

18. An applicator, as claimed in claim 1, wherein:

a cross-section of said applicator body immediately adjacent to said distal end is without curves.

* * * * *